US009613519B2

(12) United States Patent
Iseri et al.

(10) Patent No.: US 9,613,519 B2
(45) Date of Patent: Apr. 4, 2017

(54) TRACKING SYSTEM FOR HAND HYGIENE

(71) Applicant: SwipeSense, Inc., Chicago, IL (US)

(72) Inventors: Mert Iseri, Evanston, IL (US); Yuri Malina, Evanston, IL (US); Jori Hunter Hardman, Chicago, IL (US)

(73) Assignee: SWIPESENSE, INC., Chicago, IL (US)

( * ) Notice: Subject to any disclaimer, the term of this patent is extended or adjusted under 35 U.S.C. 154(b) by 0 days.

(21) Appl. No.: 15/030,926

(22) PCT Filed: Oct. 24, 2014

(86) PCT No.: PCT/US2014/062229
§ 371 (c)(1),
(2) Date: Apr. 21, 2016

(87) PCT Pub. No.: WO2015/061718
PCT Pub. Date: Apr. 30, 2015

(65) Prior Publication Data
US 2016/0267772 A1    Sep. 15, 2016

Related U.S. Application Data

(60) Provisional application No. 61/895,759, filed on Oct. 25, 2013.

(51) Int. Cl.
*G08B 21/24* (2006.01)
*G06F 15/173* (2006.01)
*H04L 29/08* (2006.01)

(52) U.S. Cl.
CPC ..... *G08B 21/245* (2013.01); *G06F 15/17331* (2013.01); *H04L 67/1097* (2013.01)

(58) Field of Classification Search
CPC .... G08B 21/245; A47K 5/1217; G06F 19/327
See application file for complete search history.

(56) References Cited

U.S. PATENT DOCUMENTS 7,855,651 B2    12/2010    LeBlond et al.
8,294,585 B2    10/2012    Barnhill
(Continued)

OTHER PUBLICATIONS

International Search Report and Written Opinion, Application No. PCT/US2014/062229; 14 pages, Feb. 3, 2015.
(Continued)

*Primary Examiner* — Curtis Odom
(74) *Attorney, Agent, or Firm* — Baker Botts L.L.P.

(57) ABSTRACT

In accordance with some embodiments of the present disclosure, a system for tracking hand hygiene may comprise a plurality of dispensers, each dispenser configured to detect a hand-hygiene event and wirelessly transmit hand-hygiene event information associated with the hand-hygiene event. The system may also include a room hub configured to wirelessly transmit location information. Further, the system may include a user circuit module configured to wirelessly receive the hand-hygiene event information, wirelessly receive the location information, and store the hand-hygiene event information, a first time stamp associated with the hand-hygiene event information, the location information, and a second time stamp associated with the location information, in a memory. The user circuit module may also be configured to transmit the hand-hygiene event information, the first time stamp, the location information, the second time stamp, and a user identifier to a central server.

40 Claims, 4 Drawing Sheets

(56) References Cited

U.S. PATENT DOCUMENTS

| | | |
|---|---|---|
| 8,564,431 B2 | 10/2013 | Snodgrass |
| 2013/0122807 A1* | 5/2013 | Tenarvitz ............. H04B 5/0031 455/41.1 |
| 2013/0250823 A1 | 9/2013 | Gaylard et al. |
| 2013/0262034 A1 | 10/2013 | Iseri et al. |
| 2014/0266730 A1 | 9/2014 | Hines et al. |

OTHER PUBLICATIONS

International Preliminary Report on Patentability, Application No. PCT/US2014/062229; 8 pages, Apr. 26, 2016.

\* cited by examiner

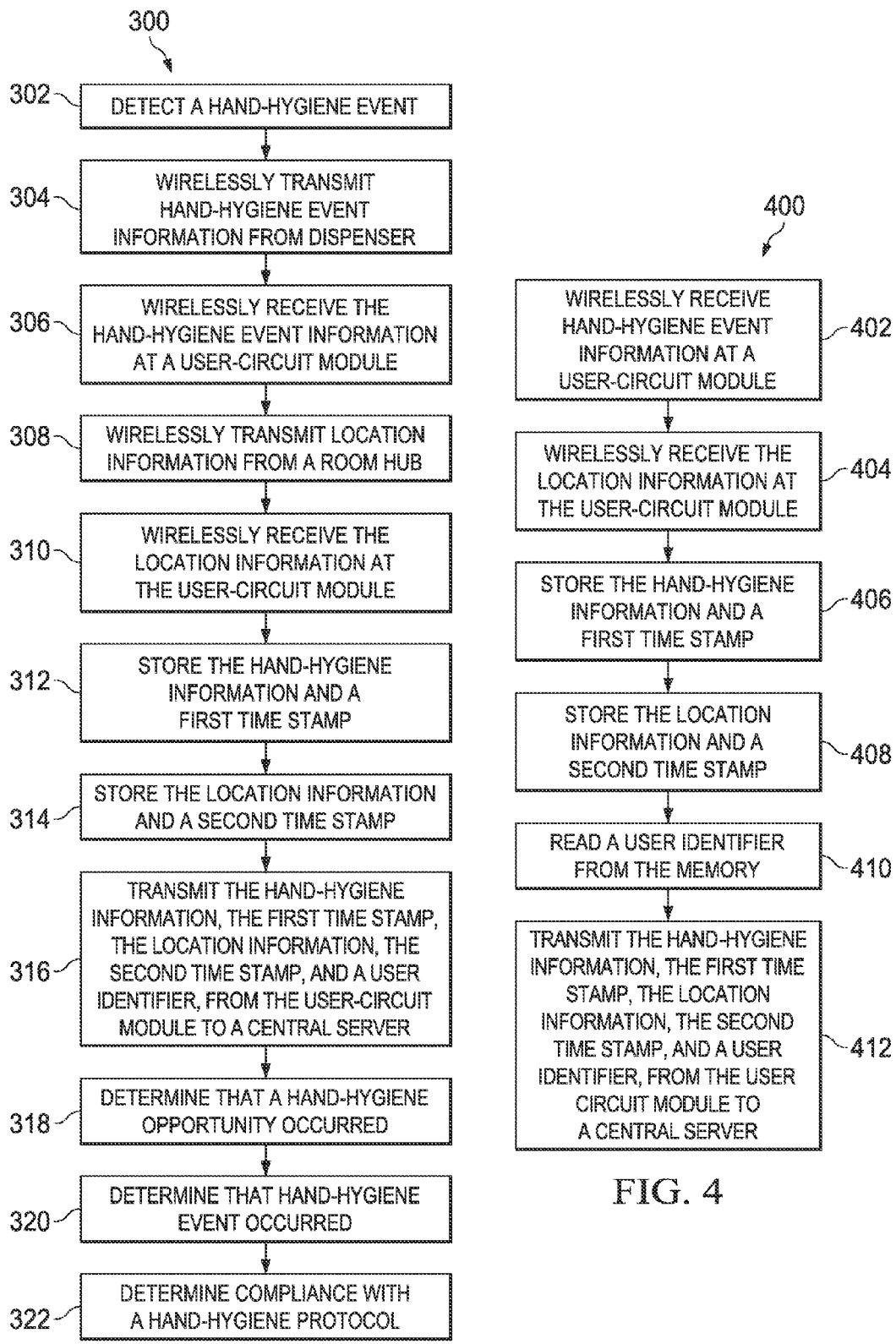

TRACKING SYSTEM FOR HAND HYGIENE

RELATED APPLICATIONS

This application is a U.S. National Stage Application of International Application No. PCT/US2014/062229 filed Oct. 24, 2014, which designates the United States, and claims the benefit of U.S. Provisional patent application Ser. No. 61/895,759, filed Oct. 25, 2013, the contents of which are incorporated by reference in their entirety.

TECHNICAL FIELD

The present disclosure relates generally to hand hygiene and more particularly to a system for tracking hand hygiene.

BACKGROUND

Hand hygiene is critical to preventing the spread of infection, germs, and/or disease, for example, in the hospital environment. Many hospitals and other health care facilities implement hand sanitization protocols under which hospital and other health care workers are required to wash or sanitize their hands at regular intervals or during certain actions such as entering a patient's room. In order to maintain compliance with such protocols, hospital workers and other health care workers may have convenient access to hand sanitizers.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 3 illustrates a flow chart of an exemplary method for tracking hand hygiene; and FIG. 4 illustrates a flow chart of an exemplary method for tracking hand hygiene.

DETAILED DESCRIPTION

In accordance with the teachings of the present disclosure, a system and method for tracking hand hygiene is provided.

Figure 1A:
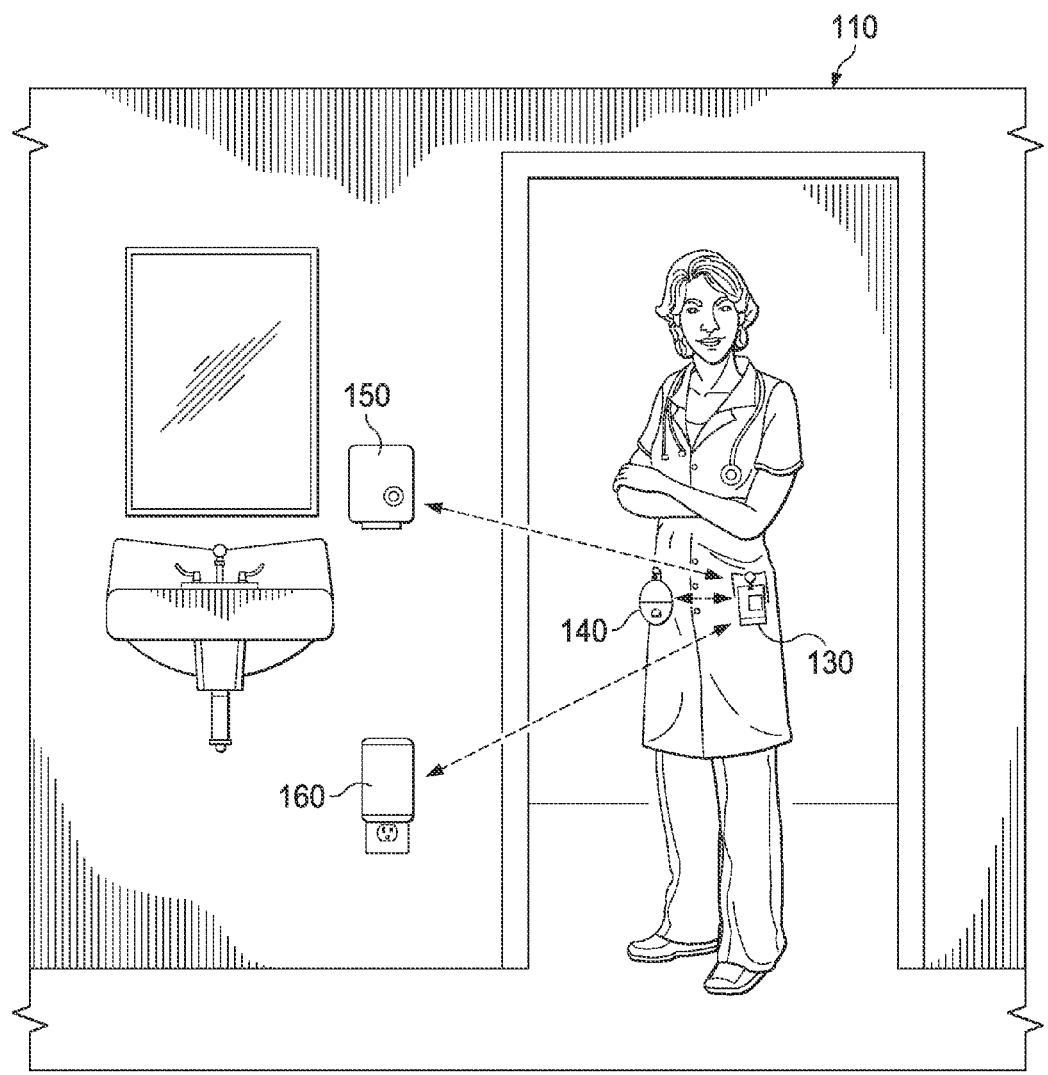
FIGS. 1A and 1B illustrate exemplary components of a system for tracking hand hygiene.
Figure 1B:
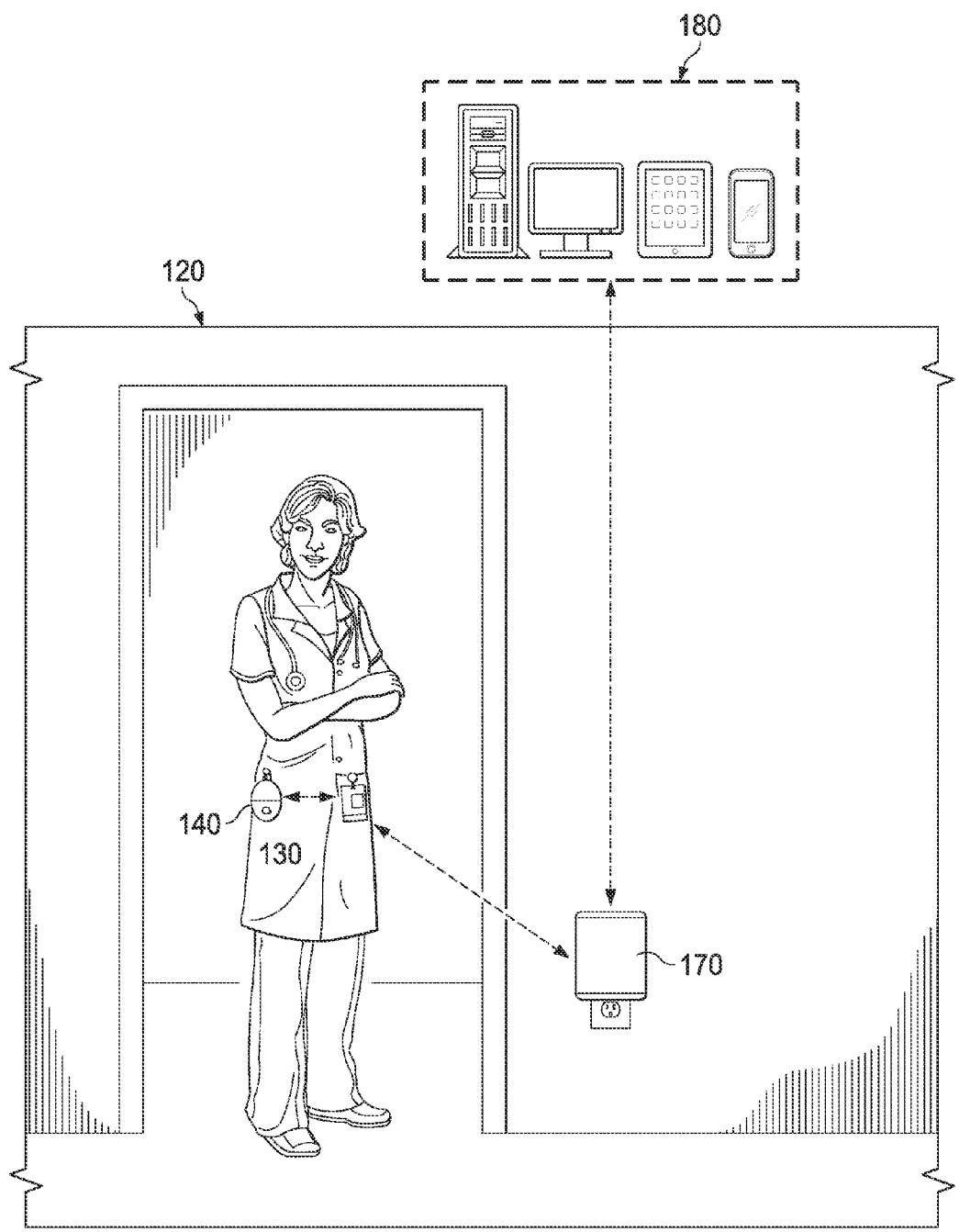

FIGS. 1A and 1B illustrate exemplary components of a system for tracking hand hygiene. As shown in FIG. 1A, a system for tracking hand hygiene may include portable dispenser 140, stationary dispenser 150, room hub 160, and badge 130. As shown in FIG. 1B, a system for tracking hand hygiene may also include master hub 170 and central server 180.

A hospital worker may be assigned an instance of badge 130, which may identify that particular hospital worker in a system for tracking hand hygiene. For example, each hospital worker using the system for tracking hand hygiene may be assigned a unique badge 130. As described below with reference to FIG. 1A, badge 130 may be utilized to collect information regarding the occurrence of hand-hygiene events (e.g., an employee sanitizing their hands with either soap or sanitizer). And, as described below with reference to FIG. 1B, badge 130 may also be used to relay the collected information to central server 180.

As shown in FIG. 1A, a hospital worker, such as a doctor or a nurse, may visit patient room 110. Entering into patient room 110 may represent a hand-hygiene opportunity for a hospital worker. For example, the hospital worker may sanitize their hands using soap or sanitizer from stationary dispenser 150 or portable dispenser 140. Although this disclosure may describe the tracking of hand hygiene in an environment such as a hospital, the system for tracking hand hygiene may be implemented by users in any suitable setting. For example, the system for tracking hand hygiene may be implemented in a doctor's office, a clinic, an outpatient surgery center, an urgent care center, a restaurant, or any other medical or non-medical environment where hand hygiene may be of interest.

Stationary dispenser 150 may be configured to dispense a dose of hand sanitizer or soap to a user (e.g., a hospital worker) when the user presses a dispensing button (or other actuator) on stationary dispenser 150. Stationary dispenser 150 may be mounted to a wall in patient room 110, placed on a table in patient room 110, or otherwise stationed in patient room 110.

Portable dispenser 140 may be carried by the hospital worker and may be configured to dispense a dose of hand sanitizer when the worker presses a dispensing button (or other actuator) of portable dispenser 140. Portable dispenser 140 may include a clip, or any other suitable attachment device, affixing portable dispenser 140 to the clothing of the hospital worker. Accordingly, portable dispenser 140 may be worn by a hospital worker and hand sanitizer may be conveniently available to that hospital worker regardless of their location within the hospital. Portable dispenser 140 may be configured to dispense doses of hand sanitizer, which may be utilized by the hospital worker at any location including or not including a washing station. Additionally, portable dispenser 140 may also be configured to dispense doses of soap. Different hospital workers may each obtain an instance of portable dispenser 140 from a commonly shared pool of available portable dispensers. For example, when one portable dispenser 140 runs out of sanitizer, malfunctions, or otherwise becomes not useful, the one portable dispenser 140 may be replaced with another portable dispenser 140 from the commonly shared pool of portable dispensers.

As described in further detail below with reference to FIG. 2, portable dispenser 140 and/or stationary dispenser 150 may wirelessly communicate with circuitry located on badge 130 after a hand-hygiene event (e.g., after the user sanitized their hands with either soap or sanitizer). Badge 130 may record the occurrence of hand-hygiene events. For example, when the hospital worker uses portable dispenser 140 to wash their hands, portable dispenser 140 and badge 130 may wirelessly communicate with each other, and badge 130 may record a hand-hygiene event. Likewise, when the hospital worker uses stationary dispenser 150 to wash their hands, stationary dispenser 150 and badge 130 may wirelessly communicate with each other, and badge 130 may record a hand-hygiene event. Because hand-hygiene events may occur utilizing either portable dispenser 140 or stationary dispenser 150, a hospital worker may participate in the system for tracking hand hygiene without necessarily carrying their own portable dispenser 140. As described in more detail below with reference to FIG. 2, badge 130 may also generate and record a time stamp associated with the hand-hygiene event information. Accordingly, badge 130 may store hand-hygiene event information indicating that the hospital worker (to whom badge 130 may be assigned)

sanitized their hands, as well as timing information regarding when the hospital worker sanitized their hands.

Badge 130 may also wirelessly communicate with room hub 160. Room hub 160 may be assigned to patient room 110, and may include a location identifier associated with patient room 110. For example, each patient room 110 in a hospital or hospital ward may include an instance of room hub 160 that uniquely identifies that patient room. Although FIG. 1A illustrates room hub 160 in patient room 110, an instance of room hub 160 may be placed in one section of a shared patient room, and another instance of room hub 160 may be placed in another section of the shared patient room. In addition, room hub 160 may be placed in any other location of interest within, for example, a hospital (e.g., an emergency room, a waiting room, a triage station, an office, or a nurse's station). When the hospital worker enters patient room 110, room hub 160 may communicate location information, including its location identifier, to badge 130. In turn, badge 130 may record the location information. As described in more detail below with reference to FIG. 2, badge 130 may also generate and record a time stamp associated with the location information. Accordingly, badge 130 may store location information indicating which patient room 110 the hospital worker (to whom badge 130 is assigned) visited, as well as timing information regarding when the hospital worker visited that patient room 110.

As shown in FIG. 1B, a system for tracking hand hygiene may also include master hub 170 and central server 180. As described in further detail below with reference to FIG. 2, badge 130 may wirelessly communicate with master hub 170 to relay stored hand-hygiene event information and location information to central server 180. For example, master hub 170 may be located at nurse station 120 or any other central service base for multiple patient rooms 110. Badge 130 may collect and store multiple instances of hand-hygiene event information (e.g., the worker washing or sanitizing their hands), and multiple instances of location information, as the hospital worker visits different patient rooms 110. Subsequently, when the hospital worker visits or walks past nurse station 120, badge 130 may communicate the stored hand-hygiene event information and the stored location information to master hub 170. Master hub 170 may be communicatively coupled to central server 180 via a wired and/or wireless connection, and may relay the hand-hygiene event information and the location information from badge 130 to central server 180. For the purposes of the present disclosure, a transmission from badge 130 (or components of badge 130) to central server 180 may refer to either the transmission of information from badge 130 to central server 180 directly, as well as the transmission of information from badge 130 to central server 180 via master hub 170 or any other suitable intermediary.

Master hub 170 may relay hand-hygiene event information and location information from multiple instances of badge 130, each assigned to different respective hospital workers, to central server 180. Accordingly, information regarding hand hygiene for multiple hospital workers may be gathered at central server 180, and compliance with hand-hygiene protocols by multiple hospital workers may be monitored.

Figure 2:
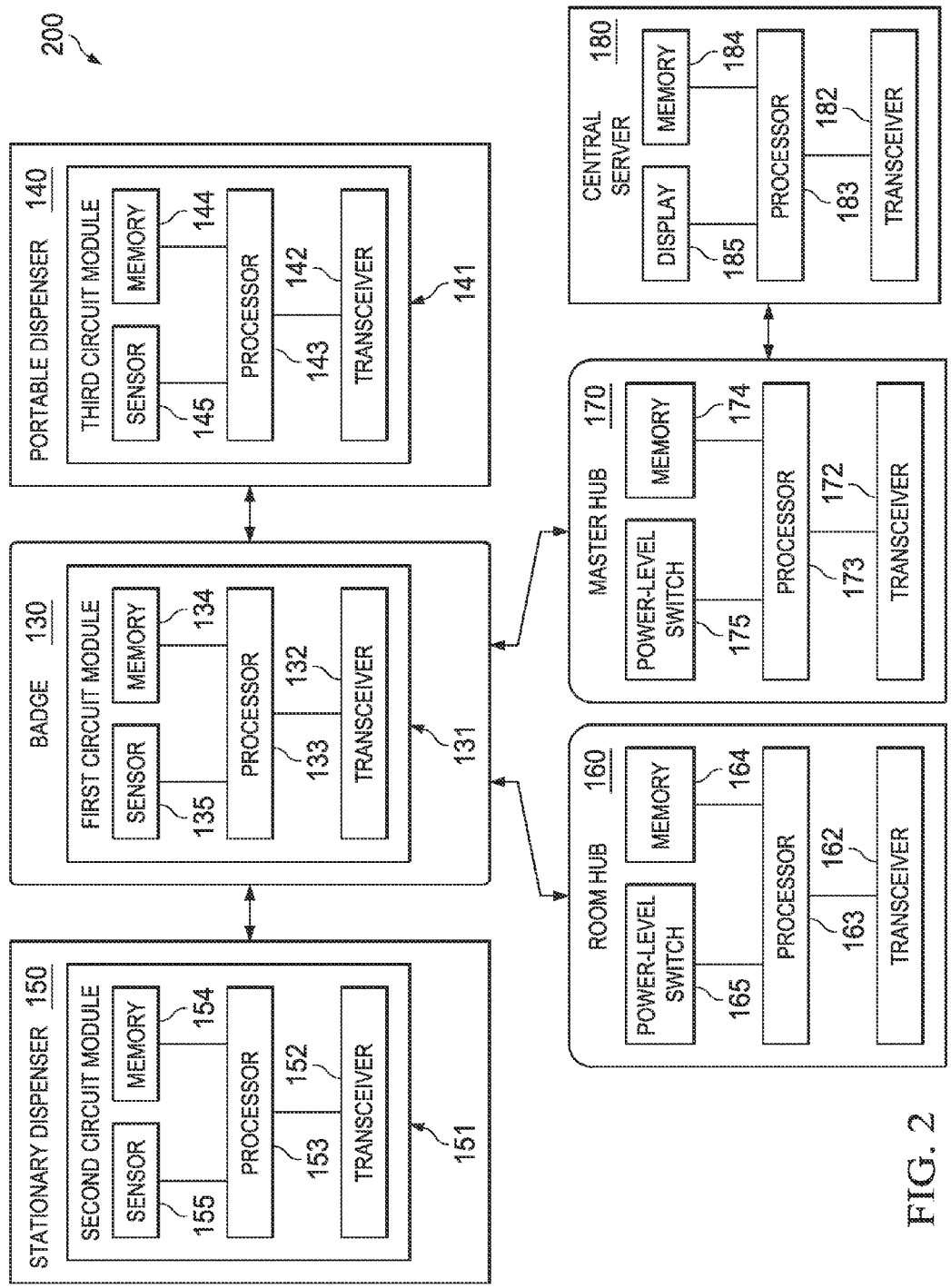
FIG. 2 illustrates a block diagram of an exemplary system for tracking hand hygiene.

FIG. 2 illustrates a block diagram of an exemplary system for tracking hand hygiene. As shown in FIG. 2, system 200 may include badge 130, portable dispenser 140, stationary dispenser 150, room hub 160, master hub 170, and central server 180.

Badge 130 may include first circuit module 131. Although first circuit module 131 is described herein as being located on badge 130, first circuit module 131 may be located on, affixed to, or incorporated within, any wearable device such as an identity ("ID") tag, a key fob, or a pin. Different instances of badge 130, each including a different instance of first circuit module 131, may be assigned to different individual users, such as hospital workers. Alternatively, different instances of first circuit module 131 alone may be assigned to different individual users. Each instance of first circuit module 131 may include a user identifier associated with the assigned user. This assignment may be stored in central server 180. First circuit module 131 may be configured to collect information about hand-hygiene events and to relay such information to central server 180. The assignment of the first circuit module 131 (or the assignment of badge 130 including first circuit module 131) to an individual may allow system 200 to associate the individual hospital worker with future hand-hygiene events collected by first circuit module 131 and relayed to central server 180. For the purposes of the present disclosure, first circuit module 131 may also be referred to as the "user circuit module."

First circuit module 131 of badge 130 may include transceiver 132, processor 133, memory 134, and sensor 135. Transceiver 132 may be a wireless transceiver, and first circuit module 131 may utilize transceiver 132 to wirelessly communicate with other components of system 200 (e.g., portable dispenser 140, stationary dispenser 150, room hub 160, and master hub 170). Processor 133 may include, for example, a microprocessor, microcontroller, digital signal processor (DSP), application specific integrated circuit (ASIC), or any other digital or analog circuitry configured to interpret and/or execute program instructions and/or process data. In some embodiments, processor 133 may interpret and/or execute program instructions and/or process data stored in memory 134. Memory 134 may be configured in part or whole as application memory, system memory, or both. Memory 134 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of first circuit module 131, for example configurations of components such as transceiver 132, may reside in memory 134 for execution by processor 133.

First circuit module 131 of badge 130 may be designed to periodically switch from a default OFF state (e.g., a low power sleep mode) to an ON state (e.g., a transmission mode) in order to determine whether an instance of stationary dispenser 150 or portable dispenser 140 having hand-hygiene event information, or whether an instance of room hub 160 having location information, is nearby. For example, at a first interval (e.g., approximately one-half second, approximately two seconds, approximately four seconds), first circuit module 131 may temporarily wake up from a low-power sleep mode and may broadcast or transmit a ping signal (e.g., a beacon signal) to determine whether an active portable dispenser 140 or an active stationary dispenser 150 is nearby. Circuitry in portable dispenser 140 and stationary dispenser 150 may normally reside in a low-power sleep mode, but may enter an active mode in response to a hand-hygiene event (e.g., a hospital user using the dispenser to sanitize their hands). Accordingly, portable dispenser 140 or stationary dispenser 150 that has recently been used by a hospital worker to wash their hands may respond to the ping signal to indicate to first circuit module 131 that a hand-hygiene event has occurred. In other words, first circuit module 131 may act as a beacon requesting hand-hygiene event information, and instances of portable dispenser 140 and stationary dispenser 150 activated by a recent hand-hygiene event may act as a reflector beacon responding with hand-hygiene event information.

First circuit module 131 of badge 130 may also temporarily wake up from a low-power sleep mode at a second interval (e.g., approximately one second, approximately four seconds, approximately ten seconds) and may broadcast or transmit a ping signal (e.g., a beacon signal) to determine whether an instance of room hub 160 is nearby. Room hub 160 may respond to the ping signal to provide a location identifier to first circuit module 131. In other words, the first circuit module 131 may act as a beacon requesting location information, and room hub 160 may act as a reflector beacon responding with location information. The first interval at which first circuit module 131 wakes up from a low-power sleep mode to ping portable dispenser 140 and/or stationary dispenser 150 may be the same or different from the second interval at which first circuit module 131 wakes up from the low-power sleep mode to ping room hub 160. Moreover, first circuit module 131 may communicate with portable dispenser 140 and/or stationary dispenser 150 on one wireless communication channel, and may communicate with room hub 160 on a separate wireless communication channel.

First circuit module 131 of badge 130 may also temporarily wake up from a low-power sleep mode at a third interval (e.g., approximately two seconds, approximately ten seconds, approximately twenty seconds) and may broadcast or transmit a ping signal (e.g., a beacon signal) to determine whether an instance of master hub 170 is nearby. Master hub 170 may respond to the ping signal with an acknowledgement signal, indicating that master hub 170 is ready to receive, from first circuit module 131, hand-hygiene event information and location information that first circuit module 131 may have collected and stored. Upon receiving the acknowledgement signal from master hub 170, first circuit module 131 may transmit any hand-hygiene event information and location information first circuit module 131 may have collected and stored.

The third interval at which first circuit module 131 wakes up from a low-power sleep mode to ping master hub 170 may be the same or different than the first interval at which first circuit module 131 wakes up to ping portable dispenser 140 and/or stationary dispenser 150 and the second interval at which first circuit module 131 wakes up to ping room hub 160. Moreover, first circuit module 131 may communicate with master hub 170 on a wireless communication channel separate from the one or more wireless communication channels used by first circuit module 131 to communicate with portable dispenser 140, stationary dispenser 150, and room hub 160.

First circuit module 131 of badge 130 may be battery operated. By periodically switching between an ON state (e.g. a transmission mode) and an OFF state (e.g., a low-power sleep mode), first circuit module 131 may conserve energy. For example, in the ON state, components of first circuit module 131 may be fully powered, and transceiver 132 of first circuit module 131 may be allowed to transmit and receive information. In the OFF state, first circuit module 131 may be in a low-power sleep mode where some components of first circuit module 131 may be inactive to conserve power while basic operations of processor 133 remain active to perform required functions such as sensing code interrupts and keeping the time of day. Accordingly, first circuit module 131 may collect hand-hygiene event information and/or location information in an energy efficient manner, thus resulting in a long lasting operation.

To further conserve power, first circuit module 131 of badge 130 may switch between an active state and an inactive state. For example, sensor 135 may be an accelerometer or any other sensor configured to detect motion. When sensor 135 detects motion, first circuit module 131 may enter an active state, during which first circuit module 131 may actively alternate between the ON state and the OFF state. However, if no motion is detected for a threshold amount of time (e.g., approximately 5 minutes, approximately 10 minutes, approximately 1 hour), first circuit module 131 may enter an inactive state. During the inactive state, first circuit module 131 may operate in a deep sleep mode (without alternating between the ON state and the OFF state) until motion is again detected by sensor 135.

First circuit module 131 of badge 130 may include a timing circuit. For example, the timing circuit may be embodied within processor 133 of first circuit module 131. The timing circuit may include a clock and may be configured to generate time stamps (e.g., a Unix time stamp or a POSIX time stamp). First circuit module 131 may add a time stamp to, or associate a time stamp with, each instance of hand-hygiene event information received from portable dispenser 140 and stationary dispenser 150, and each instance of location information received from room hub 160. The clock of first circuit module 131 may be configured to operate independently as a real time clock. Alternatively, the clock may be configured to receive periodic time updates from a master clock (e.g., a real time clock contained within master hub 170 or central server 180) and to track the time in between such periodic updates. Accordingly, the clock of the timing circuit may be implemented with an inexpensive clock circuit that would otherwise drift over time but maintains a high level of accuracy via periodic updates from the master clock.

First circuit module 131 of badge 130 may also include memory 134. Different instances of badge 130, each including a different instance of first circuit module 131, may be assigned to different users, such as hospital workers. To facilitate the identification of different hospital workers in system 200, first circuit module 131 may include a user identifier, which may be stored in memory 134. First circuit module 131 may also store hand-hygiene event information received from one or more dispensers (e.g., portable dispenser 140 or stationary dispenser 150) in memory 134. Likewise, first circuit module 131 may store location information received from room hub 160 in memory 134. First circuit module 131 may also store time stamps associated with each instance of hand-hygiene event information and each instance of location information in memory 134. As described in further detail below with reference to master hub 170, first circuit module 131 may transmit information stored in memory 134 when first circuit module 131 establishes a communication link with master hub 170. For example, when first circuit module 131 establishes a communication link with master hub 170, first circuit module 131 may transmit one or more instances of stored hand-hygiene event information, one or more instances of stored location information, time stamps associated with the hand-hygeine event information and the location information, as well as the user identifier, to master hub 170.

System 200 may include one or more instances of stationary dispenser 150. Stationary dispensers 150 may be, for example, wall-mounted dispensers located in each room of a hospital for communal use among multiple hospital workers. Although referred to herein as stationary, stationary dispensers 150 need not be affixed to a location, and may include for example dispensers placed on a table or next to a sink in a hospital room for communal use by hospital workers or others who may be in that room. Stationary dispensers 150 may be configured to dispense any suitable type (e.g., foam, gel, or liquid) of soap or sanitizer to users. Further, each stationary dispenser 150 may be provided with an instance of second circuit module 151, which may facilitate tracking of the usage details of that dispenser. For example, stationary dispenser 150 may be manufactured to include second circuit module 151. Stationary dispenser 150 may also be a pre-existing or already-installed dispenser to which second circuit module 151 may be retrofitted. For the purposes of the present disclosure, second circuit module 151 may also be referred to as a "dispenser circuit module" or a "stationary-dispenser circuit module."

Second circuit module 151 of stationary dispenser 150 may include transceiver 152, processor 153, memory 154, and sensor 155. Transceiver 152 may be a wireless transceiver, and second circuit module 151 may utilize transceiver 152 to wirelessly communicate with other components of system 200 (e.g., first circuit module 131 of badge 130). Processor 153 may include, for example, a microprocessor, microcontroller, digital signal processor (DSP), application specific integrated circuit (ASIC), or any other digital or analog circuitry configured to interpret and/or execute program instructions and/or process data. In some embodiments, processor 153 may interpret and/or execute program instructions and/or process data stored in memory 154. Memory 154 may be configured in part or whole as application memory, system memory, or both. Memory 154 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of second circuit module 151, for example configurations of components such as transceiver 152, may reside in memory 154 for execution by processor 153.

Second circuit module 151 may include sensor 155 to detect a user dispensing soap or sanitizer from stationary dispenser 150. Sensor 155 may include any one or a combination of a button, a magnetic actuator, a switch, a tilt sensor, or an infrared (IR) motion sensor. For example, sensor 155 may include a tilt sensor paired with a motion-detecting IR sensor. Second circuit module 151 may be attached to or integrated within stationary dispenser 150 (e.g., a wall-mounted dispenser) at a suitable position to allow sensor 155 to detect a hand-hygiene event (e.g., the dispensing of soap or sanitizer). When the user (e.g., a hospital worker) dispenses soap or sanitizer, sensor 155 may detect the hand-hygiene event and may communicate that event to processor 153. In turn, processor 153 may place second circuit module 151 into an active ON state in which transceiver 152 may be turned on. When second circuit module 151 is in an active ON state, transceiver 152 may respond to a ping signal (e.g., a request signal) from first circuit module 131 in badge 130 by sending an acknowledgement signal (e.g., an acknowledgement packet) back to first circuit module 131. Second circuit module 151 may also send the hand-hygiene event information to first circuit module 131, either as a part of, or separate from, the acknowledgement signal. As described above with reference to first circuit module 131, first circuit module 131 may store the hand-hygiene event information and later transmit the hand-hygiene event information via master hub 170 to the central server 180 for further analysis.

Second circuit module 151 of stationary dispenser 150 may be battery operated. Second circuit module 151 may switch between a default OFF state (e.g., a low power sleep mode) and an ON state (e.g., a transmission mode) due to the sensing of a hand-hygiene event. When second circuit module 151 is in an ON state, second circuit module 151 may respond to a ping signal from first circuit module 131 of badge 130 with hand-hygiene event information indicating that the sensed hand-hygiene event occurred. Second circuit module 151 may remain ON for an amount of time required to establish a communication link with first circuit module 131. For example, second circuit module 151 may remain ON for an amount of time that may be predetermined based on the characteristics of the communication channel between first circuit module 131 and second circuit module 151. In addition, second circuit module 151 may remain ON until confirming that the hand-hygiene event information was successfully transmitted to first circuit module 131. Second circuit module 151 may then return to an OFF state (e.g., a low power sleep mode) until another hand-hygiene event is sensed.

By switching between the ON and OFF states based on sensed hand-hygiene events, second circuit module 151 of stationary dispenser 150 may conserve energy. For example, in the ON state, components of second circuit module 151 may be fully powered, and transceiver 152 may be fully operational. In the OFF state, second circuit module 151 may be in a deep sleep mode whereby some components of second circuit module 151 may be inactive to conserve power while basic operations of processor 153 and sensor 155 remain active to perform functions such as sensing hand-hygiene events. Accordingly, second circuit module 151 may provide hand-hygiene event information to system 200 in an energy efficient manner, resulting in a long lasting operation.

The hand-hygiene event information transmitted from second circuit module 151 of stationary dispenser 150 may include any suitable amount of information regarding the sensed hand-hygiene event. For example, the hand-hygiene event information may include an indicator that a hand-hygiene event occurred. The hand-hygiene event information may additionally include hygiene-type information including, but not limited to, the dispenser type (e.g., stationary or portable), the type of sanitizing substance used during the hand-hygiene event (e.g., soap or sanitizer), as well as the form of the sanitizing substance used during the hand-hygiene event (e.g., liquid, gel, foam). The hygiene-type information may be stored in second circuit module 151 in any suitable manner. For example, the hygiene-type information may be hard coded in second circuit module 151 or may be programmed into memory 154 of second circuit module 151.

In some embodiments, the hand-hygiene event information from second circuit module 151 of stationary dispenser 150 may additionally include a location identifier and/or a unique dispenser identifier, which may be stored in memory 154 of second circuit module 151. Central server 180 may be programmed to associate the unique dispenser identifier with information such as the location of stationary dispenser 150 and/or the hygiene-type of stationary dispenser 150.

Stationary dispenser may be a pre-existing dispenser that may be retrofitted with second circuit module 151. Second circuit module 151 may be reconfigurable to alter its hygiene-type information and/or its unique dispenser identifier. Accordingly, a single instance of second circuit module 151 may be configured with a first set of hygiene-type information and/or unique dispenser identifier information when fitted to a first instance of stationary dispenser 150, and may be configured with a second set of hygiene-type information and/or unique dispenser identifier information when fitted to a second instance of stationary dispenser 150.

System 200 may include one or more instances of portable dispenser 140. For example, different instances of portable dispenser 140 may be worn by different individual users and may each include a clip configured to attach portable dispenser 140 to the user or the clothing of the user. Each portable dispenser 140 may include an instance of third circuit module 141, which may facilitate tracking of the usage details of that portable dispenser 141. For the purposes of the present disclosure, third circuit module 141 may also be referred to as a "dispenser circuit module" or a "portable-dispenser circuit module."

Third circuit module 141 of portable dispenser 140 may include transceiver 142, processor 143, memory 144, and sensor 145. Transceiver 142 may be a wireless transceiver, and third circuit module 141 may utilize transceiver 142 to wirelessly communicate with other components of system 200 (e.g., first circuit module 131 of badge 130). Processor 143 may include, for example, a microprocessor, microcontroller, digital signal processor (DSP), application specific integrated circuit (ASIC), or any other digital or analog circuitry configured to interpret and/or execute program instructions and/or process data. In some embodiments, processor 143 may interpret and/or execute program instructions and/or process data stored in memory 144. Memory 144 may be configured in part or whole as application memory, system memory, or both. Memory 144 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of third circuit module, for example configurations of components such as transceiver 142, may reside in memory 144 for execution by processor 143.

Third circuit module 141 may include sensor 145 to detect a user dispensing soap or sanitizer from portable dispenser 140. When the user dispenses soap or sanitizer from portable dispenser 140, sensor 145 may detect a hand-hygiene event and may communicate that event to processor 143. In turn, processor 143 may place third circuit module 141 into an active ON state, in which transceiver 142 may respond to a ping signal (e.g., a request signal) from first circuit module 131 of badge 130 by sending an acknowledgement signal (e.g., an acknowledgement packet) back to first circuit module 131. Third circuit module 141 may send the hand-hygiene event information to first circuit module 131, either as a part of, or separate from, the acknowledgement signal. As described above with reference to first circuit module 131, first circuit module 131 may then store the hand-hygiene event information and later transmit the stored hand-hygiene event information via master hub 170 to central sever 180 for further analysis.

Third circuit module 141 of portable dispenser 140 may be battery operated. Third circuit module 141 may switch between a default OFF state (e.g., a low power sleep mode) and an ON state (e.g., a transmission mode) due to the sensing of a hand-hygiene event. When third circuit module 141 is in an ON state, third circuit module 141 may respond to a ping signal from first circuit module 131 with hand-hygiene event information indicating that the sensed hand-hygiene event occurred. Third circuit module 141 may remain ON for an amount of time required to establish a communication link with first circuit module 131. For example, third circuit module 141 may remain ON for an amount of time that may be predetermined based on the characteristics of the communication channel between first circuit module 131 and third circuit module 141. Alternatively, third circuit module 141 may remain ON until confirming that the hand-hygiene event information was successfully transmitted to first circuit module 131 of badge 130. Third circuit module 141 may then return to an OFF state (e.g., a low power sleep mode) until another hand-hygiene event is sensed.

By switching between such states based on sensed hand-hygiene events, third circuit module 141 of portable dispenser 140 may conserve energy. For example, in the ON state, components of third circuit module 141 may be fully powered, and transceiver 142 may be fully operational. In the OFF state, third circuit module 141 may be in a deep sleep mode whereby some components of third circuit module 141 may be inactive to conserve power while basic operations of processor 143 and sensor 145 remain active to perform functions such as sensing hand-hygiene events. Accordingly, third circuit module 141 may provide hand-hygiene event information to the system in an energy efficient manner, resulting in a long lasting operation.

The hand-hygiene event information transmitted from third circuit module 141 of portable dispenser 140 may include any suitable amount of information regarding the sensed hand-hygiene event. For example, the hand-hygiene event information may include an indicator that a hand-hygiene event occurred. The hand-hygiene event information may additionally include hygiene-type information including, but not limited to, the dispenser type (e.g., stationary or portable), the type of sanitizing substance used during the hand-hygiene event (e.g., soap or sanitizer), as well as the form of the sanitizing substance used during the hand-hygiene event (e.g., liquid, gel, foam). The hygiene-type information may be stored in third circuit module 141 in any suitable manner. For example, the hygiene-type information may be hard coded in third circuit module 141 or may be programmed into memory 144 of third circuit module 141.

System 200 may include one or more instances of room hub 160. For example, an instance of room hub 160 may be placed in each patient room in a hospital. Instances of room hub 160 may be utilized to communicate location information to first circuit module 131 of badge 130. Instances of room hub 160 may be placed in any location of interest within, for example, a hospital (e.g., a patient room, an emergency room, a waiting room, a triage station, an office, or a nurse's station).

Room hub 160 may include transceiver 162, processor 163, memory 164, and power-level switch 165. Room hub 160 may utilize transceiver 162 to wirelessly communicate with other components of system 200 (e.g., first circuit module 131 of badge 130). Processor 163 may include, for example, a microprocessor, microcontroller, digital signal processor (DSP), application specific integrated circuit (ASIC), or any other digital or analog circuitry configured to interpret and/or execute program instructions and/or process data. In some embodiments, processor 163 may interpret and/or execute program instructions and/or process data stored in memory 164. Memory 164 may be configured in part or whole as application memory, system memory, or both. Memory 164 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of room hub 160, for example configurations of components such as transceiver 162, may reside in memory 164 for execution by processor 163.

Memory 164 of room hub 160 may be hard-coded or programmable. Further, memory 164 may include a hard-coded or a programmed location identifier (e.g., the room number of a hospital patient room). In some embodiments, the location identifier may be a unique room-hub identifier, which central server 180 may associate with a given location (e.g., a specific hospital room).

Transceiver 162 may respond to a ping signal (e.g., a request signal) from first circuit module 131 of badge 130 by sending an acknowledgement signal (e.g., an acknowledgement packet) to first circuit module 131. Transceiver 162 may send location information, including the location identifier of room hub 160, to first circuit module 131. Transceiver 162 may send the location information either as a part of, or separate from, the acknowledgement signal. As described above with reference to first circuit module 131, first circuit module 131 may then store the location information and later transmit the location information via master hub 170 to the central sever 180 for further analysis.

Room hub 160 may also include power-level switch 165, which may be utilized to adjust the wireless signal range of transceiver 162. Accordingly, the wireless signal range of room hub 160 may be set lower when room hub 160 is located in a small room, and may be set higher when room hub 160 is located in a larger room. Power-level switch 165 may allow the wireless signal range of room hub 160 to be adjusted such that the wireless signal range of room hub 160 in one room does not overlap in an interfering manner with the wireless signal range of room hub 160 in an adjacent room.

Room hub 160 may be battery operated or may be plugged into an electrical wall outlet. Room hub 160 may be configured to always operate in an ON state (e.g., in a transmission mode), for example, in embodiments in which room hub is plugged into an electrical outlet. Room hub 160 may also be configured to periodically alternate between an ON state (e.g., in a transmission mode) and an OFF state (e.g., a low-power sleep mode) in order to conserve energy, for example, in embodiments in which room hub 160 is battery operated.

System 200 may include one or more instances of master hub 170. For example, an instance of master hub 170 may be placed in a central location (e.g., at a nurse station) within a premise in which system 200 is deployed. First circuit module 131 of badge 130 may collect and store multiple instances of hand-hygiene event information and location information as a hospital worker sanitizes their hands while visiting and administering care in different patient rooms. Subsequently, master hub 170 may be utilized to relay the stored hand-hygiene event information and location information (as well as associated time stamps) from first circuit module 131 to central server 180.

Master hub 170 may include transceiver 172, processor 173, and memory 174. Master hub 170 may utilize transceiver 172 to wirelessly communicate with other components of system 200 (e.g., first circuit module 131 of badge 130). Master hub 170 may also utilize transceiver 172 to communicate over either a wired connection or a wireless connection with central server 180. Processor 173 may include, for example, a microprocessor, microcontroller, digital signal processor (DSP), application specific integrated circuit (ASIC), or any other digital or analog circuitry configured to interpret and/or execute program instructions and/or process data. In some embodiments, processor 173 may interpret and/or execute program instructions and/or process data stored in memory 174. Memory 174 may be configured in part or whole as application memory, system memory, or both. Memory 174 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of master hub, for example configurations of components such as transceiver 172, may reside in memory 174 for execution by processor 173.

First circuit module 131 of badge 130 may periodically transmit a ping signal (e.g., a beacon signal) to determine whether master hub 170 is nearby. When a hospital worker comes within the wireless signal range of master hub 170, master hub 170 may respond to the ping signal with an acknowledgement signal (e.g., an acknowledgement packet), indicating that master hub 170 is ready to receive information from first circuit module 131. Master hub 170 may also include power-level switch 175, which may be utilized to adjust the wireless signal range of transceiver 172. Upon receiving the acknowledgement signal from master hub 170, first circuit module 131 may transmit one or more instances of stored hand-hygiene event information, one or more instances of location information, time stamps associated with the hand-hygiene event information and the location information, as well as a user identifier, to master hub 170. Master hub 170 may, in turn, communicate this data to central server 180.

As described above with reference to first circuit module 131, first circuit module 131 of badge 130 may include a clock that may receive periodic time updates from a master clock (e.g., a real time clock contained within master hub 170 or central server 180) and may track the time in between such periodic updates. For example, when first circuit module 131 sends a ping signal to master hub 170, and master hub 170 sends an acknowledgement signal back to first circuit module 131, master hub 170 may also send a time update to first circuit module 131 that may accurately reflect the time kept by the master clock of system 200 in central server 180 and/or master hub 170. Accordingly, the clock of first circuit module 131 may be implemented with an inexpensive clock circuit that would otherwise drift over time but maintains a high level of accuracy via the periodic updates from the master clock of system 200.

Although master hub 170 may be described herein as a separate device from room hub 160, in some embodiments, each room hub 160 within tracking system 200 may operate both as a room hub as described herein, and as a master hub as described herein.

System 200 may include central server 180. Central server 180 may include transceiver 182, processor 183, memory 184, and display 185. Processor 183 may include, for example, a microprocessor, microcontroller, digital signal processor (DSP), application specific integrated circuit (ASIC), or any other digital or analog circuitry configured to interpret and/or execute program instructions and/or process data. In some embodiments, processor 183 may interpret and/or execute program instructions and/or process data stored in memory 184. Memory 184 may be configured in part or whole as application memory, system memory, or both. Memory 184 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of central server 180, for example configurations of components such as transceiver 182, may reside in memory 184 for execution by processor 183.

Central server 180 may receive instances of hand-hygiene event information, instances of location information, as well as a user identifier and time stamps associated with each instance of hand-hygiene event information and location information. Processor 183 may record this data into memory 184, from which the data may be subsequently accessed for analysis. For the purposes of the present disclosure, a receipt of information by central server 180 from badge 130 (or components of badge 130) may refer to either the receipt of information by central server 180 directly from badge 130, as well as the receipt of information by central server 180 directly from badge 130 via master hub 170 or any other suitable intermediary.

Central server 180 may track location information for a hospital worker (as identified by the user identifier) over time to determine the number of patient rooms visited by the hospital worker over a period of time (e.g., over a work shift). The hospital worker's location information may be combined with hand-hygiene event information for a hospital worker (as identified by the user identifier) to determine when and where that worker sanitized their hands. Moreover, such tracking may be performed for multiple hospital workers who may each be assigned their own unique badge 130 and/or first circuit module 131. Accordingly, central server 180 may generate a number of hand-hygiene statistics that may be compared to various hand-hygiene protocols. For example, central server 180 may track whether one or more hospital workers sanitized their hands every time they entered a patient room. Likewise, central server 180 may calculate the rate at which one or more hospital workers sanitized their hands over a given period of time, and may track whether that rate meets a required sanitizing frequency, e.g., at least once every thirty minutes. Further, central server 180 may calculate the number of times a user sanitized their hands over a period of time, e.g., a shift of a hospital worker.

Central server 180 may collect and communicate such statistics to display 185. Display 185 may include any display suitable to communicate the collected statistics to one or more hospital workers who may use the information. For example, in some embodiments, display 185 may be a computer monitor in a hospital administrator's office, a doctor's office, or at a nurse station. Accordingly, the hospital administrator may view the collected hand-hygiene statistics and may monitor the hand-hygiene compliance of the hospital's workers. In addition, hospital workers may view the collected hand-hygiene statistics and may monitor their own hand-hygiene compliance. Central server 180 may also generate a hand-hygiene practice compliance report and suggest remedial actions for those who do not comply with hand-hygiene protocols.

Although, first circuit module 131 of badge 130 may include a user identifier that may be used to associate hand-hygiene event information and location information with a particular hospital worker, system 200 may also be configured such that individual users are anonymous. For example, central server 180 may be configured to ignore the user identifiers associated with hand-hygiene event information and location information it receives. As another example, first circuit module 131 may be configured with no user identifier. For such embodiments, compliance data for a group of hospital workers as a whole may be retrieved and reports may be generated with respect to the entire group of users within a hospital unit implementing system 200.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such as wires, optical fibers, and other electromagnetic and/or optical carriers; and/or any combination of the foregoing.

As described above with reference to FIG. 2, various components of system 200 including first circuit module 131 of badge 130, second circuit module 151 of stationary dispenser 150, third circuit module 141 of portable dispenser 140, room hub 160, master hub 170, and central server 180, may communicate wirelessly with each other. For the purposes of the present disclosure, a wireless connection or wireless communication between two or more transceivers of the above listed devices may occur according to ANT, Bluetooth, Wi-Fi, GSM, CDMA, or any other suitable wireless, or micro-power wireless, communication protocol. Further, any of the described wireless communication links may be supplemented with or replaced by a wired communication link, and may utilize any suitable LAN, WAN, Internet, or other network protocol.

FIG. 3 illustrates a flow chart of an exemplary method 300 for tracking hand hygiene. Method 300 may start, and at step 302, a hand-hygiene event may be detected. For example, a hospital worker may walk into patient room 110 and may sanitize their hands with either soap or sanitizer. If the hospital worker washes their hands with soap and/or sanitizer dispensed from stationary dispenser 150, second circuit module 151 of stationary dispenser 150 may detect the hand-hygiene event. Likewise, if the hospital worker sanitizes their hands with soap and/or sanitizer dispensed from portable dispenser 140, third circuit module 141 of portable dispenser 140 may detect the hand-hygiene event.

At step 304, hand-hygiene event information may be wirelessly transmitted, and at step 306, the hand-hygiene event information may be wirelessly received. For example, as described above with reference to FIG. 2, first circuit module 131 of badge 130 may broadcast or transmit a ping signal on a first wireless communication channel searching for an activated dispenser. If second circuit module 151 of stationary dispenser 150 detected the hand-hygiene event at step 302, then processor 153 may place second circuit module 151 into an active ON state in which transceiver 152 may be turned on. When second circuit module 151 is in an active ON state, transceiver 152 may respond to the ping signal from first circuit module 131. Second circuit module 151 may then wirelessly transmit hand-hygiene event information to first circuit module 131 indicating that the hand-hygiene event occurred, and first circuit module 131 may wirelessly receive the hand-hygiene event information.

As another example, if third circuit module 141 of portable dispenser 140 detected the hand-hygiene event at step 302, then processor 143 may place third circuit module 141 into an active ON state, in which transceiver 142 may respond to a ping signal from first circuit module 131. Third circuit module 141 may then wirelessly transmit hand-hygiene event information to first circuit module 131 indicating that the hand-hygiene event occurred, and first circuit module 131 may wirelessly receive the hand-hygiene event information.

At step 308, location information may be wirelessly transmitted, and at step 310, the location information may be wirelessly received. For example, as described above with reference to FIG. 2, first circuit module 131 may broadcast or transmit a ping signal on a second wireless communication channel searching for a nearby room hub 160. Transceiver 162 of a nearby room hub 160 may respond to the ping signal from first circuit module 131 by sending an acknowledgement signal to first circuit module 131. Transceiver 162 may send location information, including the location identifier of room hub 160, to first circuit module 131, either as a part of, or separate from, the acknowledgement signal. First circuit module 131 may then wirelessly receive the location information from transceiver 162 of room hub 160.

At step 312, the hand-hygiene event information and a first time stamp associated with the hand-hygiene event information may be stored in a memory. For example, in response to receiving the hand-hygiene event information in step 306, first circuit module 131 may generate a first time stamp and add the first time stamp to, or associate the first time stamp with, the hand-hygiene event information received at step 306. First circuit module 131 may then store the hand-hygiene event information and the associated first time stamp to memory 134.

At step 314, the location information and a second time stamp associated with the location information may be stored to a memory. For example, in response to receiving the location information in step 310, first circuit module 131 may generate a second time stamp and add the second time stamp to, or associate the second time stamp with, the location information received at step 310. First circuit module 131 may then store the location information and the associated second time stamp to memory 134.

At step 316, the hand-hygiene event information, the first time stamp, the location information, the second time stamp, and a user identifier may be transmitted to a central server. In some embodiments, the information may be transmitted from first circuit module 131, to central server 180, via a master hub 170. For example, as described above with reference to FIG. 2, first circuit module 131 may periodically transmit a ping signal on a third wireless communication channel to determine whether an instance of master hub 170 is nearby. When a hospital worker wearing badge 130 including first circuit module 131 comes within the wireless signal range of master hub 170, master hub 170 may respond to the ping signal with an acknowledgement signal, indicating that master hub 170 is ready to receive information from first circuit module 131. First circuit module 131 may then transmit the stored hand-hygiene event information, the stored location information, time stamps associated with the hand-hygiene event information and the location information, as well as a user identifier, to master hub 170. Master hub 170 may, in turn, relay this data across a wired or a wireless communication link to central server 180.

At step 318, it may be determined that a hand-hygiene opportunity occurred based on the location information. For example, based on the location information, central server 180 may determine that a hospital worker (identified by the user identifier) entered patient room 110. The entrance of the hospital worker into patient room 110 may represent a hand-hygiene opportunity for that hospital worker.

At step 320, it may be determined that a hand-hygiene event occurred based on the hand-hygiene event information. For example, based on the hand-hygiene event information, central server 180 may determine that the hospital worker identified in step 318 washed their hands.

At step 322, compliance with a hand-hygiene protocol may be determined. For example, based on the location information and the hand-hygiene event information, as well as the respective time stamps associated with the location information and the hand-hygiene event information, central server may determine that the hospital worker identified in step 318 washed their hands upon entering patient room 110, in accordance with a hand-hygiene protocol that requires hospital workers to sanitize their hands every time they enter a patient room.

Although FIG. 3 discloses a particular number of steps to be taken with respect to method 300, method 300 may be executed with greater or lesser steps than those depicted in FIG. 3. For example, method steps 302 through 316 may be repeated in response to a hospital worker sanitizing their hands multiple times as they administer care in multiple patient rooms during a work shift. In addition, although FIG. 3 discloses a certain order of steps to be taken with respect to method 300, the steps comprising method 300 may be completed in any suitable order. For example, in some embodiments, step 304 and step 306 may be completed simultaneously.

FIG. 4 illustrates a flow chart of an exemplary method for tracking hand hygiene. Method 400 may start, and at step 402, hand-hygiene event information may be wirelessly received. For example, as described above with reference to FIG. 2, first circuit module 131 may broadcast or transmit a ping signal on a first wireless communication channel searching for an activated dispenser. If second circuit module 151 of stationary dispenser 150 detected the hand-hygiene event, then processor 153 may place second circuit module 151 into an active ON state in which transceiver 152 may be turned on. When second circuit module 151 is in an active ON state, transceiver 152 may respond to the ping signal from first circuit module 131. Second circuit module 151 may then wirelessly transmit hand-hygiene event information to first circuit module 131 indicating that the hand-hygiene event occurred, and first circuit module 131 may wirelessly receive the hand-hygiene event information.

As another example, if third circuit module 141 of portable dispenser 140 detected the hand-hygiene event, then processor 143 may place third circuit module 141 into an active ON state, in which transceiver 142 may respond to a ping signal from first circuit module 131. Third circuit module 141 may then wirelessly transmit hand-hygiene event information to first circuit module 131 indicating that the hand-hygiene event occurred, and first circuit module 131 may wirelessly receive the hand-hygiene event information.

At step 404, location information may be wirelessly received. For example, as described above with reference to FIG. 2, first circuit module 131 may broadcast or transmit a ping signal on a second wireless communication channel searching for a nearby room hub 160. Transceiver 162 of a nearby room hub 160 may respond to the ping signal from first circuit module 131 by sending an acknowledgement signal to first circuit module 131. Transceiver 162 may send location information, including the location identifier of room hub 160, to first circuit module 131, either as a part of, or separate from, the acknowledgement signal. First circuit module 131 may then wirelessly receive the location information from transceiver 162 of room hub 160.

At step 406, the hand-hygiene event information and a first time stamp associated with the hand-hygiene event information may be stored to a memory. For example, in response to receiving the hand-hygiene event information in step 402, first circuit module 131 may generate a first time stamp and add the first time stamp to, or associate the first time stamp with, the hand-hygiene event information. First circuit module 131 may then store the hand-hygiene event information and the associated first time stamp to memory 134.

At step 408, the location information and a second time stamp associated with the location information may be stored to a memory. For example, in response to receiving the location information in step 404, first circuit module 131 may generate a second time stamp and add the second time stamp to, or associate the second time stamp with, the location information received. First circuit module 131 may then store the location information and the associated second time stamp to memory 134.

At step 410, a user identifier may be read from memory. Processor 133 may read a user identifier from memory 134 of first circuit module 131. The user identifier may be associated with the particular hospital worker to whom badge 130 and/or first circuit module 131 may be assigned.

At step 412, the hand-hygiene event information, the first time stamp, the location information, the second time stamp, and the user identifier may be transmitted to a central server. In some embodiments, the information may be transmitted from first circuit module 131, to central server 180, via a master hub 170. For example, as described above with reference to FIG. 2, first circuit module 131 may periodically transmit a ping signal on a third wireless communication channel to determine whether an instance of master hub 170 is nearby. When a hospital worker wearing badge 130 including first circuit module 131 comes within the wireless signal range of master hub 170, master hub 170 may respond to the ping signal with an acknowledgement signal, indicating that master hub 170 is ready to receive information from first circuit module 131. First circuit module 131 may then transmit the stored hand-hygiene event information, the stored location information, time stamps associated with the hand-hygiene event information and the location information, as well as the user identifier, to master hub 170. Master hub 170 may, in turn, relay this data across a wired or a wireless communication link to central server 180.

Although FIG. 4 discloses a particular number of steps to be taken with respect to method 400, method 400 may be executed with greater or lesser steps than those depicted in FIG. 4. For example, method steps 402 through 412 may be repeated in response to a hospital worker sanitizing their hands multiple times as they administer care in multiple patient rooms during a work shift. In addition, although FIG. 4 discloses a certain order of steps to be taken with respect to method 400, the steps comprising method 400 may be completed in any suitable order. For example, in some embodiments, step 402 and step 406 may be completed simultaneously.

Although the present disclosure has been described in detail, it should be understood that various changes, substitutions, and alterations can be made hereto without departing from the spirit and the scope of the disclosure as defined by the appended claims.

What is claimed is:

1. A system for tracking hand hygiene, comprising:
   a plurality of dispensers, each dispenser configured to:
   detect a hand-hygiene event; and
   wirelessly transmit hand-hygiene event information associated with the hand-hygiene event;
   a room hub configured to wirelessly transmit location information; and
   a user circuit module configured to:
   wirelessly receive the hand-hygiene event information from any of the plurality of dispensers;
   wirelessly receive the location information from the room hub;
   store the hand-hygiene event information and a first time stamp associated with the hand-hygiene event information in a memory;
   store the location information and a second time stamp associated with the location information in the memory; and
   transmit the hand-hygiene event information, the first time stamp, the location information, the second time stamp, and a user identifier, to a central server.

2. The system of claim 1, further comprising a master hub, wherein the user circuit module is configured to transmit the hand-hygiene event information, the first time stamp, the location information, the second time stamp, and the user identifier to the central server via the master hub.

3. The system of claim 2, wherein the user circuit module is further configured to:
   communicate with the plurality of dispensers over a first wireless communication channel;
   communicate with the room hub over a second wireless communication channel; and
   communicate with the master hub over a third wireless communication channel.

4. The system of claim 1, wherein at least one of the plurality of dispensers is a portable dispenser.

5. The system of claim 1, wherein at least one of the plurality of dispensers is a stationary dispenser.

6. The system of claim 1, wherein the hand-hygiene event information indicates the type of dispenser that generated the hand-hygiene event information.

7. The system of claim 1, wherein the hand-hygiene event information indicates the type of sanitizing substance utilized during the hand-hygiene event.

8. The system of claim 1, wherein the user circuit module is further configured to:
   generate the first time stamp in response to the receipt of the hand-hygiene event information from the dispenser; and
   generate the second time stamp in response to the receipt of the location information from the room hub.

9. The system of claim 1, wherein the central server is configured to:
   determine whether a hand-hygiene opportunity occurred based on the location information; and
   determine whether the hand-hygiene event occurred based on the hand-hygiene event information.

10. The system of claim 9, wherein the central server is further configured to determine compliance with a hand-hygiene protocol based on whether the hand-hygiene opportunity occurred and whether the hand-hygiene event occurred.

11. A method for tracking hand hygiene, comprising:
   detecting a hand-hygiene event at one of a plurality of dispensers;
   wirelessly transmitting hand-hygiene event information associated with the hand-hygiene event from the one of the plurality of dispensers;

wirelessly receiving the hand-hygiene event information at a user circuit module;
wirelessly transmitting location information from a room hub;
wirelessly receiving the location information at the user circuit module;
storing the hand-hygiene event information and a first time stamp associated with the hand-hygiene event information in a memory of the user circuit module;
storing the location information and a second time stamp associated with the location information in the memory; and
transmitting the hand-hygiene event information, the first time stamp, the location information, the second time stamp, and a user identifier from the user circuit module to a central server.

12. The method of claim 11, further comprising transmitting the hand-hygiene event information, the first time stamp, the location information, the second time stamp, and the user identifier to the central server via a master hub.

13. The method of claim 12, further comprising:
communicating between the user circuit module and the one of the plurality of dispensers over a first wireless communication channel;
communicate between the user circuit module and the room hub over a second wireless communication channel; and
communicate between the user circuit module and the master hub over a third wireless communication channel.

14. The method of claim 11, wherein the one of the plurality of dispensers is a portable dispenser.

15. The method of claim 11, wherein the one of the plurality of dispensers is a stationary dispenser.

16. The method of claim 11, wherein the hand-hygiene event information indicates the type of dispenser that generated the hand-hygiene event information.

17. The method of claim 11, wherein the hand-hygiene event information indicates the type of sanitizing substance utilized during the hand-hygiene event.

18. The method of claim 11, further comprising:
generating the first time stamp at the user circuit module in response to receiving the hand-hygiene event information from the dispenser; and
generating the second time stamp at the user circuit module in response to receiving the location information from the room hub.

19. The method of claim 11, further comprising:
determining that a hand-hygiene opportunity occurred based on the location information; and
determining that hand-hygiene event occurred based on the hand-hygiene event information.

20. The method of claim 19, further comprising determining compliance with a hand-hygiene protocol based on whether the hand-hygiene opportunity occurred and whether the hand-hygiene event occurred.

21. A device for tracking hand hygiene, comprising:
a user circuit module comprising a wireless transceiver and a memory, the wireless transceiver configured to receive hand-hygiene event information and location information;
the user circuit module configured to:
store the hand-hygiene event information, and a first time stamp associated with the hand-hygiene event information, in the memory;
store the location information, and a second time stamp associated with the location information, in the memory; and
read a user identifier from the memory;
the wireless transceiver further configured to transmit the hand-hygiene event information, the first time stamp, the location information, the second time stamp, and the user identifier to a central server.

22. The device of claim 21, wherein the hand-hygiene event information, the first time stamp, the location information, the second time stamp, and the user identifier are transmitted to the central server via a hub.

23. The device of claim 21, wherein the wireless transceiver is further configured to:
receive the hand-hygiene event information on a first wireless communication channel;
receive the location information on a second wireless communication channel; and
transmit the hand-hygiene event information, the first time stamp, the location information, the second time stamp, and the user identifier, on a third wireless communication channel.

24. The device of claim 23, wherein the wireless transceiver is further configured to:
initiate a first wireless communication link on the first wireless communication channel by periodically broadcasting a first signal on the first wireless communication channel;
initiate a second wireless communication link on the second wireless communication channel by periodically broadcasting a second signal on the second wireless communication channel; and
initiate a third wireless communication link on the third wireless communication channel by periodically broadcasting a third signal on the third wireless communication channel.

25. The device of claim 24, wherein each of the first, second, and third wireless communication links are configured according to one of the ANT, Bluetooth, and Wi-Fi communication protocols.

26. The device of claim 21, wherein the hand-hygiene event information indicates that a hand-hygiene event occurred.

27. The device of claim 21, wherein the hand-hygiene event information indicates the type of dispenser that generated the hand-hygiene event information.

28. The device of claim 21, wherein the hand-hygiene event information indicates the type of sanitizing substance utilized during a hand-hygiene event.

29. The device of claim 21, wherein the user circuit module is further configured to:
generate the first time stamp in response to receipt of the hand-hygiene event information by the wireless transceiver; and
generate the second time stamp in response to receipt of the location information by the wireless transceiver.

30. The device of claim 21, further comprising a motion sensor, wherein the user circuit module is configured to enter a low-power sleep mode in response to a lack of motion detected by the motion sensor for a threshold amount of time.

31. A method, comprising:
wirelessly receiving hand-hygiene event information and location information at a user circuit module;
storing the hand-hygiene event information, and a first time stamp associated with the hand-hygiene event information, in a memory;

storing the location information, and a second time stamp associated with the location information, in the memory;

reading a user identifier from the memory; and transmitting the hand-hygiene event information, the first time stamp, the location information, the second time stamp, and the user identifier, from the user circuit module to a central server.

32. The method of claim 31, comprising transmitting the hand-hygiene event information, the first time stamp, the location information, the second time stamp, and the user identifier from the user circuit module to the central server via a hub.

33. The method of claim 31, further comprising:

receiving the hand-hygiene event information on a first wireless communication channel;

receiving the location information on a second wireless communication channel; and transmitting the hand-hygiene event information, the first time stamp, the location information, the second time stamp, and the user identifier, on a third wireless communication channel.

34. The method of claim 33, further comprising:

initiating a first wireless communication link on the first wireless communication channel by periodically broadcasting a first signal on the first wireless communication channel;

initiating a second wireless communication link on the second wireless communication channel by periodically broadcasting a second signal on the second wireless communication channel; and initiating a third wireless communication link on the third wireless communication channel by periodically broadcasting a third signal on the third wireless communication channel.

35. The method of claim 34, wherein each of the first, second, and third wireless communication links are configured according to one of the ANT, Bluetooth, and Wi-Fi communication protocols.

36. The method of claim 31, wherein the hand-hygiene event information indicates that a hand-hygiene event occurred.

37. The method of claim 31, wherein the hand-hygiene event information indicates the type of dispenser that generated the hand-hygiene event information.

38. The method of claim 31, wherein the hand-hygiene event information indicates the type of sanitizing substance utilized during a hand-hygiene event.

39. The method of claim 31, generating the first time stamp in response to receiving the hand-hygiene event information; and generating the second time stamp in response to receiving the location information.

40. The method of claim 39, entering a low-power sleep mode based on a lack of motion detected by a motion sensor for a threshold amount of time.

* * * * *